(12) United States Patent
Kusumoto

(10) Patent No.: US 11,660,118 B1
(45) Date of Patent: May 30, 2023

(54) LEAD EXTRACTION TOOL WITH LEVER AND DOUBLE ACTION DRIVE

(71) Applicant: Walter Kusumoto, Chico, CA (US)

(72) Inventor: Walter Kusumoto, Chico, CA (US)

( * ) Notice: Subject to any disclaimer, the term of this patent is extended or adjusted under 35 U.S.C. 154(b) by 0 days.

(21) Appl. No.: 17/479,093

(22) Filed: Sep. 20, 2021

Related U.S. Application Data

(60) Provisional application No. 63/128,334, filed on Dec. 21, 2020, provisional application No. 63/080,191, filed on Sep. 18, 2020.

(51) Int. Cl.
| | | |
|---|---|---|
| *A61B 17/34* | (2006.01) | |
| *A61B 17/3205* | (2006.01) | |
| *A61B 17/00* | (2006.01) | |
| *A61N 1/362* | (2006.01) | |
| *A61N 1/39* | (2006.01) | |

(52) U.S. Cl.
CPC ...... *A61B 17/3468* (2013.01); *A61B 17/3205* (2013.01); *A61N 1/362* (2013.01); *A61B 2017/0042* (2013.01); *A61B 2017/00367* (2013.01); *A61N 1/3956* (2013.01)

(58) Field of Classification Search
CPC ............ A61B 17/3468; A61B 17/3205; A61B 17/320758; A61B 17/3207; A61B 17/320783; A61B 17/34; A61B 2017/320775; A61B 2017/320766
See application file for complete search history.

(56) References Cited

U.S. PATENT DOCUMENTS

2008/0039884 A1 * 2/2008 Nohilly ............ A61B 17/32002
606/180

OTHER PUBLICATIONS

Cook Medical; Evolution System for Lead Extraction; www.cookmedical.com; May 31, 2019.

* cited by examiner

*Primary Examiner* — Majid Jamialahmadi
(74) *Attorney, Agent, or Firm* — Heisler & Associates

(57) ABSTRACT

A lead extraction tool includes a lever for enhanced mechanical advantage. A belt of the tool which causes rotation of a cutter on an end of a sheath can be driven both when a trigger of the handheld tool is squeezed and when the trigger is relaxed. A pair of winged engagers are carried upon a pedestal which moves with the trigger, with a driver coupled to a portion of the trigger causing a rear winged engager or a front winged engager to engage the belt, both when squeezing the trigger and when relaxing the trigger.

9 Claims, 8 Drawing Sheets

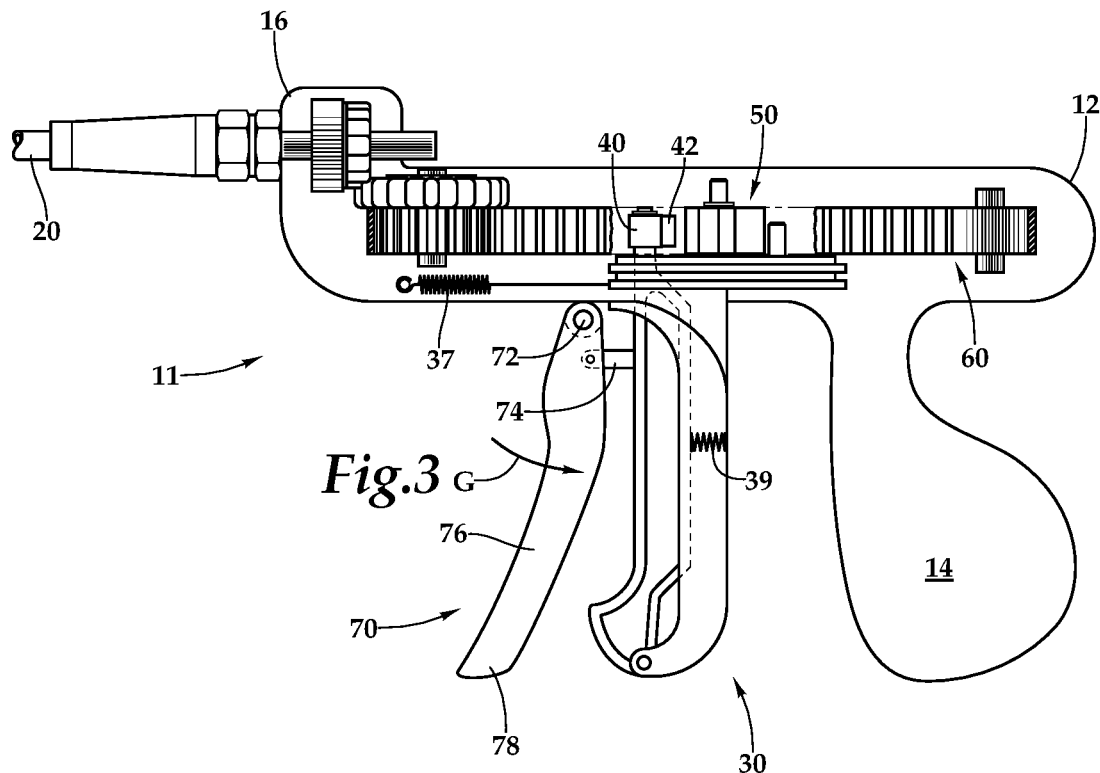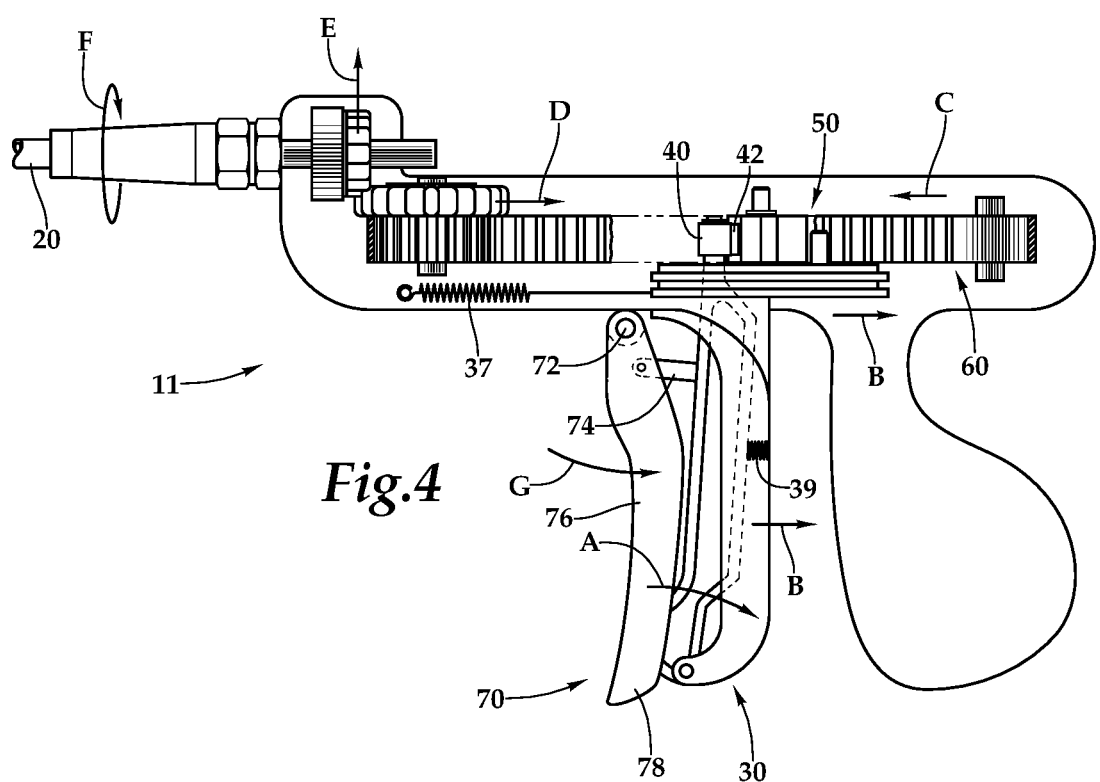

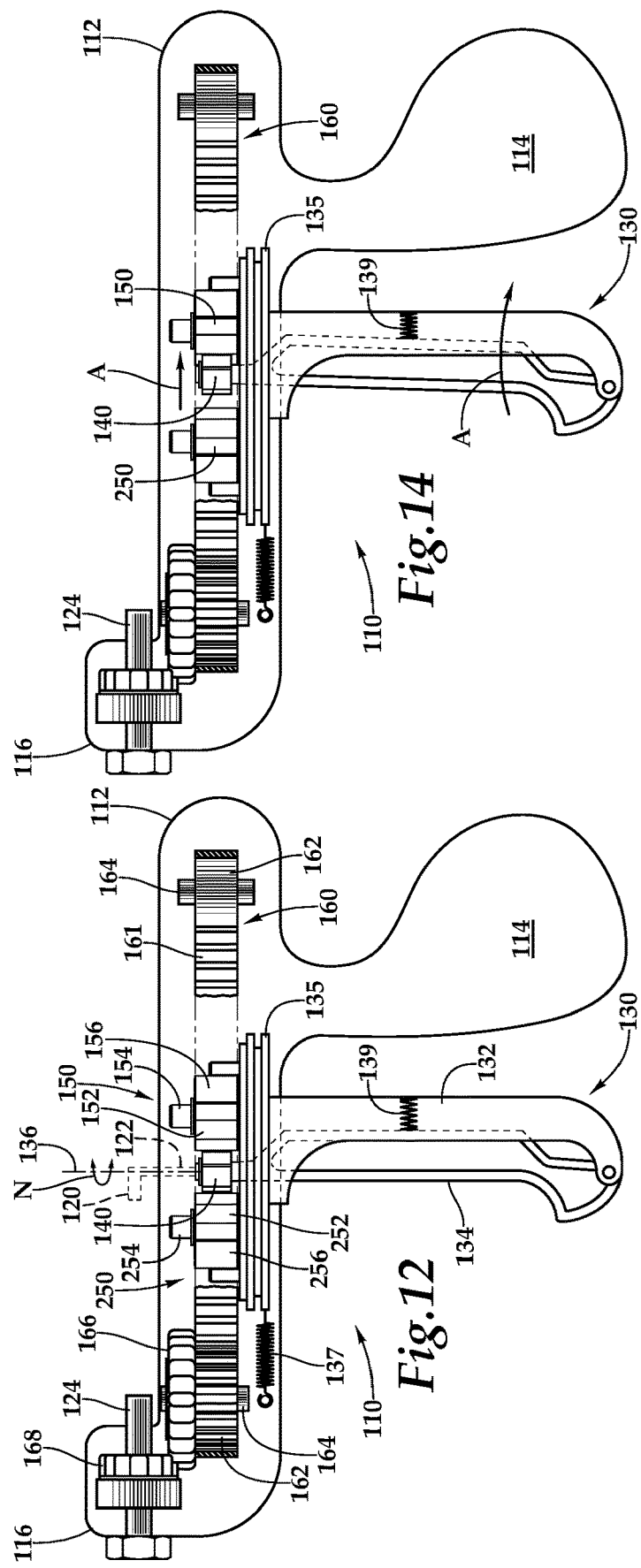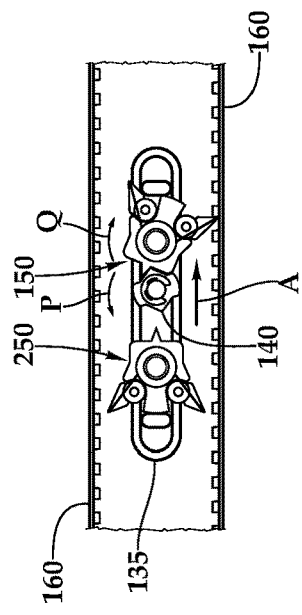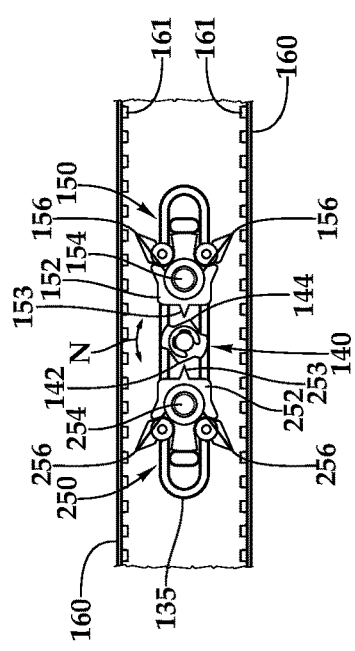

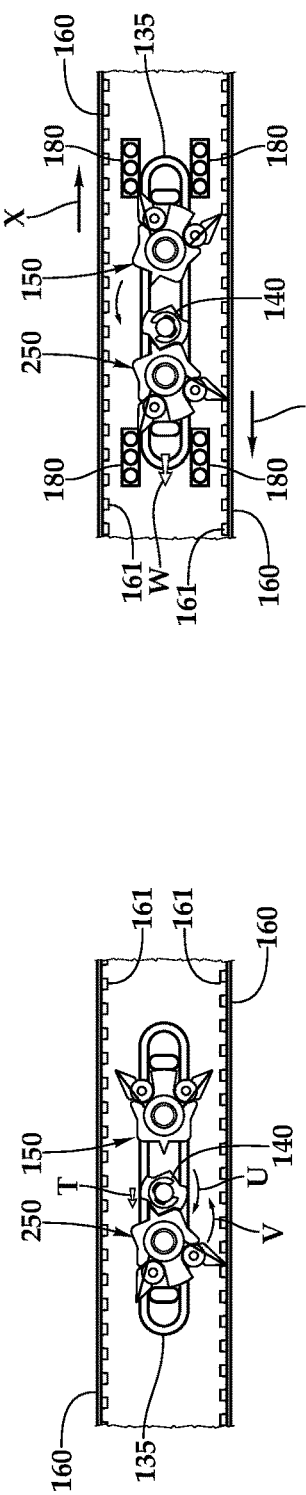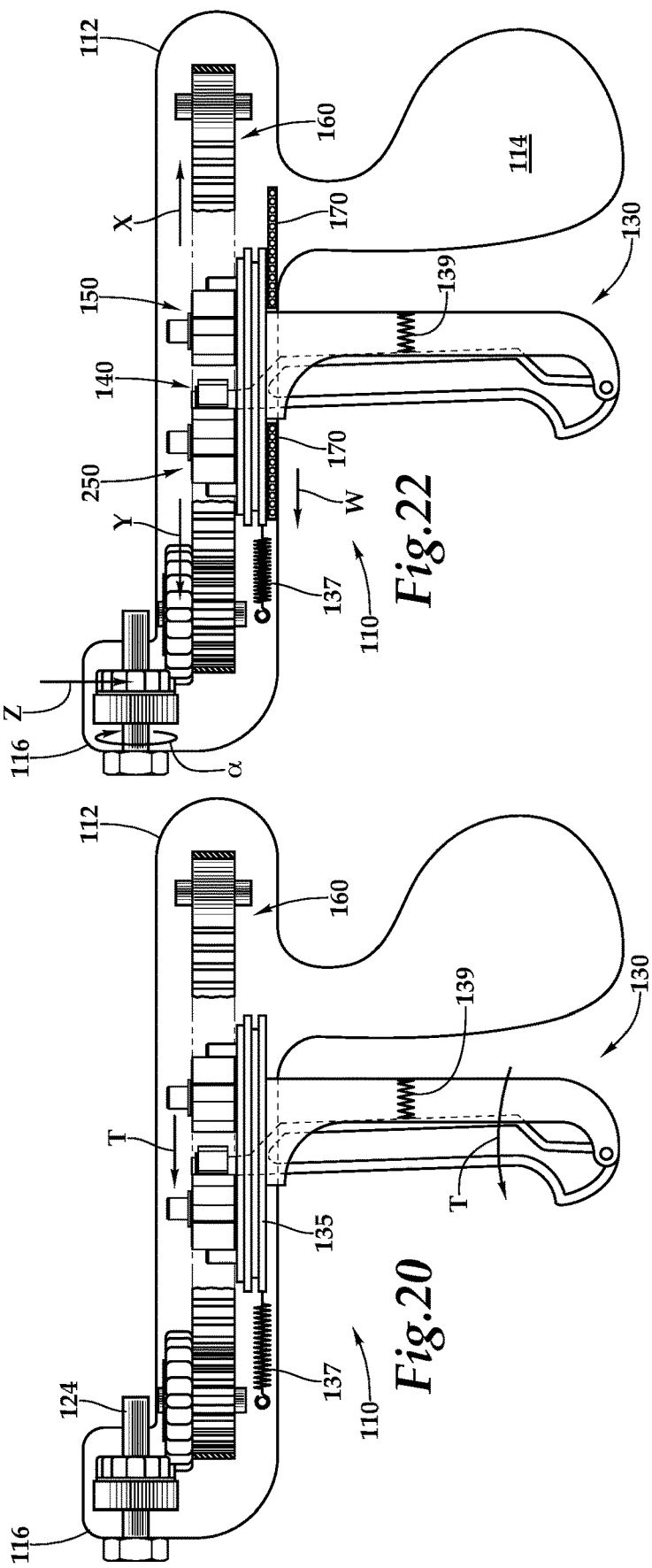

LEAD EXTRACTION TOOL WITH LEVER AND DOUBLE ACTION DRIVE

CROSS-REFERENCE TO RELATED APPLICATIONS

This application claims benefit under Title 35, United States Code § 119(e) of U.S. Provisional Application No. 63/080,191 filed on Sep. 18, 2020 and U.S. Provisional Application No. 63/128,334 filed on Dec. 21, 2020.

FIELD OF THE INVENTION

The following invention relates to medical devices to assist in separating pacemaker leads and defibrillator leads from attachment points, such as within portions of a patient's heart. More particularly, this invention relates to handheld tools with rotary sheaths for use in cardiac lead extraction medical procedures.

BACKGROUND OF THE INVENTION

Intracardiac devices such as pacemakers and implantable cardiac defibrillators are a cornerstone in arrhythmia care. The majority of devices have a pulse generator and a lead which travels in the intravascular space to the heart. On relatively frequent occasions, these leads become infected or malfunction, and warrant removal. Two companies, Cook Medical and Spectranetics have lead removal technologies which use mechanical disruption of tissue to remove leads. Both lead extraction systems use locking stylets that enter the lead body for traction purposes, to both remove the lead and to allow for a rail for a sheath to travel along the length of the lead. Both systems have rotational extraction sheaths which are shaped like a gun, with a rotating cutter/blade at the tip. This technology requires the operator to manually squeeze a trigger repeatedly to rotate the bladed tip which is followed by a relaxation phase where the trigger returns to the ready state. This procedure requires repeated hand squeezing which can cause fatigue and skin irritation to the operator.

Particular details of one such prior art lead extraction tool are described herein and provided by Cook Medical Technologies LLC of Bloomington, Ind. under the trademark "Evolution." This prior art device (illustrated in FIGS. 1 and 2 herein) is a handheld manually operated tool 10. The tool 10 includes a housing 12 which covers and protects internal moving elements of the tool 10. A grip 14 acts as a handle and is sized and shaped to conveniently rest within a palm of a hand of a user. A head/barrel 16 is at an upper forward-most portion of the tool 10. This head/barrel supports a sheath 20 and a cutter 26 at a tip of the sheath 20, while operation of the tool causes the sheath 20 and associated cutter 26 to rotate (along arrow F of FIG. 2). A coupling 22 couples the sheath 20 to an output shaft 24 of the tool 10. A trigger assembly 30 of the tool 10 is actuated to cause sheath 20 and cutter 26 rotation through an intervening mechanism.

In this particular embodiment, the trigger assembly 30 includes a sliding main trigger 32 with a pivoting trigger 34 pivoted to the sliding main trigger 32. Thus, the trigger assembly 30 has two degrees of freedom including a sliding/translation movement and a pivoting movement. Rotation of the pivoting trigger 34 (along arrow A of FIG. 2) causes associated pivoting of a trigger axis 36 and movement of a driver 40 secured to this pivoting trigger 34 by a rod 38 therebetween. The driver 40 is allowed to rotate somewhat upon this rod 38, as well as pivoting (along arrow A) with motion of the pivoting trigger 34.

The driver 40 is part of a squeeze engaging system along with a winged engager 50 just to a rear of the driver 40 and a belt/tread 60 surrounding the driver 40 and winged engager 50. The winged engager 50 is rotatably mounted to a pedestal 35 which is secured to the sliding main trigger 32, so that the pedestal 35 slides (along arrow B) when the sliding main trigger 32 is moved by fingers of a user squeezing the trigger assembly 30, while gripping the grip 14 of the housing 12. The belt 60 is separately rotatably supported by the housing 12, so that the driver 40 and winged engager 50 move relative to the belt 60. A spring 37 and bias spring 39 bias the different parts of the trigger assembly 30 toward an original position, but allow for movement of the sliding main trigger 32 and associated pedestal 35 and winged engager 50, as well as pivoting of the pivoting trigger 34 and associated driver 40.

The driver 40 includes a point 42 on a side of the driver 40 facing the winged engager 50. When the driver 40 is rotated and moved rearwardly (along arrow A of FIG. 2) it impacts the winged engager 50. Such impact causes the winged engager 50 to rotate relative to the pedestal 35 so that a wing of the winged engager 50 engages with teeth 61 on an inside of the belt 60. This engagement of the winged engager 50 with teeth 61 of the belt 60 is caused to occur by rotation of the pivoting trigger 34 and driver 40 (along arrow A of FIG. 2). Further actuation of the trigger assembly 30 results in sliding action of the sliding main trigger 32 (along arrow B of FIG. 2) which causes the pedestal 35 and winged engager 50 to move rearwardly. With a wing of the winged engager 50 engaging a tooth 61 of the belt 60, such translation of the winged engager 50 and pedestal 35 causes the belt 60 to be carried rearwardly on a side of the belt 60 which is engaged by the wing of the winged engager 50.

In the depiction shown in FIG. 2, such engagement between the wing of the winged engager 50 and the belt 60 is on a left side of the belt 60 (when viewed from above and forcing the head/barrel 16. With the left side of the belt 60 moving really, the right side of the belt 60 is caused to move forwardly (along arrow C of FIG. 2). This is because the belt 60 is carried upon pulleys 62 pivotably supported upon axles 64 oriented substantially vertically relative to the housing 12 and at forward and rearward portions of the housing 12. An input gear 66 is supported by a forward one of the pulleys 62. An output gear 68 is provided perpendicular to the input gear 66 and centered upon the output shaft 24 which is coupled to the sheath 20 through the coupling 22. Thus, as the belt 60 moves, the gears 66, 68 are caused to also move (along arrows D and E of FIG. 2) resulting in rotation (along arrow F) of the sheath 20 and cutter 26.

After the squeeze engaging system has been fully squeezed, the sheath 20 stops rotating. Release of the trigger assembly 30 by fingers of a user allows for the spring 37 and bias spring 39 to cause the pedestal 35 and winged engager 50 to return forward to an original position, and for the driver 40 and associated pivoting trigger 34 to rotate back to an original position relative to the sliding main trigger 32. The trigger assembly 30 is thus positioned to again be squeezed to repeat the process and have the sheath 20 and associated cutter 26 rotate again as the trigger assembly 30 is squeezed.

While generally effective, this tool requires a large number of repeated squeeze and release cycles to manually rotate the cutter 26 and to advance through tissue or other materials which may have attached to the lead which is to be extracted, which lead may have been static within the body of the patient for many years. Extraction of the lead is a delicate procedure. However, surgeons or other medical professionals experience significant hand fatigue when utilizing the prior art tool 10, decreasing the degree to which care and precision can be exercised when wielding the tool. Accordingly, a need exists for a modified lead extraction tool, and/or accessories for attachment to the tool 10 or similar tools to cause the tool 10 to be easier to use and requiring less energy and less time to effectively utilize such a lead extraction tool.

SUMMARY OF THE INVENTION

With this invention, a rotational sheath lever system to make the trigger pull phase more efficient, and a dual pull system which rotates the extraction sheath blades bidirectionally, during both the squeeze and relax phase of trigger pull. In addition or by itself, a lever can be added (or substitute parts of the squeeze engaging system) to more easily cause the sheath and outer tip of the lead extraction tool to rotate.

In one embodiment, a lever is added to the trigger system to allow force to be concentrated closer to the trigger center of body, which allows for more efficient delivery of rotational torque sheath and to the outer tip. The lever allows the entire force of the hand be concentrated to a proximal portion of the trigger, for more efficient translation of energy. In such an iteration, a distal portion of the trigger requires less force to moving the trigger and creating rotational torque more easily than with squeezing the trigger directly.

There are multiple types of levers that could be used, depending on the location of the fulcrum. The lever could be of a compound lever type, where the fulcrum is on the trigger mechanism itself. The lever could also be a simple lever. The fulcrum of the lever can be on the trigger mechanism within the housing or outside the housing of the extraction tool. The fulcrum can be on the trigger wherever it is considered to be the most advantageous. The lever can be any curve or be straight. The lever would push onto the main trigger, which would bring the whole trigger mechanism closer to the handle. The spring could also be relocated on the opposite side of the trigger mechanism or multiple springs can be provided to properly bias the trigger to an unsqueezed position.

In one embodiment, the lever replaces the trigger mechanism, with the lever directly driving the belt to turn the gears, to finally turn the sheath. A spring brings the lever back to a resting state. The fulcrum can be on the trigger wherever is the most advantageous. The lever can be any curve or be straight. The attachment to the belt could be fixed or a similar attachment as in the current relax/attach mechanism currently being utilized. The attachment to the belt could have a rotational or a slide relationship with the lever as it moves back and forth. The attachment to the belt could have an additional spring mechanism, so that for each squeeze, the belt is driven farther, and produces more physical work.

As another option according to this invention, the tool 10 described in detail in the background above and in FIGS. 1 and 2 is modified so that the squeeze engaging mechanism produces rotation of the sheath 20 and cutter 26 both when squeezing the trigger assembly 30 and also when releasing the trigger assembly. In this way, only half as many "squeezes" of the trigger assembly are required to experience the same amount of cutting action. To achieve this, a second winged engager is provided forward of the driver and the driver is modified to include both a forward point and a rearward point. The spring is provided to be strong enough that it causes engagement of the belt/tread and rotation of the associated gears to cause rotation of the sheath 20 and cutter 26 while the trigger assembly is being relaxed back to its original position. The surgeon or other user controls this return stroke of the trigger assembly to correspondingly control action of the cutter 26 during this return stroke of the trigger assembly. Other modifications can place the relax engagement system in various locations and springs of various types (tension, compression, torsion or check springs) can be used to selectively store and release energy to drive the belt and in turn the sheath and cutter tip.

OBJECTS OF THE INVENTION

Accordingly, a primary object of the present invention is to provide a lead extraction tool which utilizes a lever system to provide enhanced mechanical advantage for operation of the lead extraction tool.

Another object of the present invention is to provide a lead extraction tool which is easier to operate and requires less energy and less force for operation of a rotating cutter at an end of a rotating sheath thereof.

Another object of the present invention is to enhance the precision and dexterity with which a surgeon or other medical professional can wield a manual cardiac lead extraction tool.

Another object of the present invention is to provide a manual lead extraction tool which can rotate a cutter at an end of a sheath both while pulling a trigger of the tool and while relaxing a trigger of the tool, such that a similar amount of cutting can be achieved with only half as many cycles of pulling and releasing the trigger.

Another object of the present invention is to provide a lead extraction tool which induces less fatigue upon a hand of a surgeon or other medical professional while performing a typical cardiac lead extraction procedure.

Another object of the present invention is to provide a lead extraction tool which can separate a lead from attached tissues more quickly than with prior art extraction tools.

Another object of the present mention is to provide a lead extraction tool which can separate a lead from attached tissues more easily than with prior art extraction tools.

Another object of the present invention is to provide a lead extraction tool which can separate a lead from attached tissues with greater control over operation of the tool than with prior art lead extraction tools.

Another object of the present invention is to provide accessories for modification to an existing lead extraction tool to enhance ease of use, speed and control for a user of the tool.

Another object of the present invention is to provide a method for lead extraction which causes less fatigue for a user, and can be more precisely controlled than with prior art extraction methods.

Other further objects of the present invention will become apparent from a careful reading of the included drawing figures, the claims and detailed description of the invention.

BRIEF DESCRIPTION OF THE DRAWINGS

FIG. 3 is a front elevation view similar to that which is shown in FIG. 2, but with the tool modified to include an auxiliary lever to provide additional mechanical advantage and ease in actuating a trigger assembly of the tool.

FIG. 4 is a front elevation view of that which is shown in FIG. 3, but after the lever has been rotated and the trigger assembly has been actuated through action of the lever thereon, according to one embodiment of this invention.

FIG. 11 is a top plan view of a squeeze engaging system according to an alternative embodiment of that which is shown in FIGS. 1 and 2 depicting the prior art, and with the squeeze engaging system particularly including both a rearward winged engager and a forward winged engager, for engaging with the belt both during squeezing of the trigger and relaxing of the trigger to provide a double acting lead extraction tool.

FIG. 12 is a front elevation view of a double acting lead extraction tool in a position corresponding with the squeeze engaging system of FIG. 11.

FIG. 13 is a top plan view similar to that which is shown in FIG. 11, but after the trigger assembly begins to be actuated.

FIG. 14 is a front elevation view of that which is shown in FIG. 13, and also including surrounding elements of the entire tool other than the sheath.

FIG. 19 is a top plan view similar to that which is shown in FIG. 17, but showing how further relaxing of the trigger assembly causes the relax engaging mechanism to again engage with a portion of the belt to be ready for driving of the belt during further relaxation and return of the trigger assembly to an original position.

FIG. 20 is a front elevation view of that which is shown in FIG. 19, and also including surrounding elements of the entire tool other than the sheath.

FIG. 21 is a top plan view similar to that which is shown in FIG. 19, and showing how the relax engaging mechanism is engaged with the belt and advances the belt during completion of the return stroke of the trigger assembly back to its original position.

FIG. 22 is a front elevation view of that which is shown in FIG. 21, and also including surrounding elements of the entire tool other than the sheath.

DESCRIPTION OF THE PREFERRED EMBODIMENT

Figure 1:
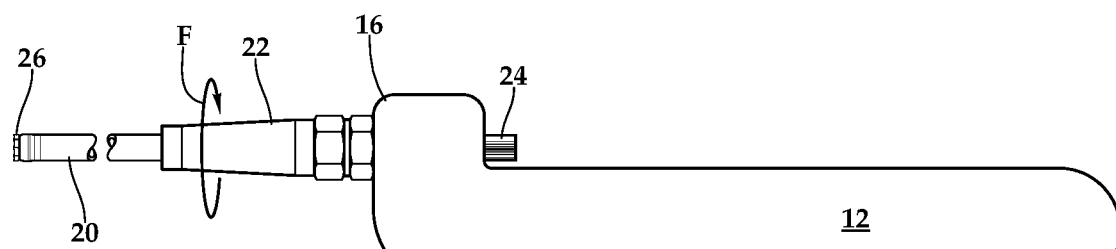
FIG. 1 is a front elevation view of a prior art lead extraction tool which is modified according to various embodiments of this invention in following figures and/or as described in the written description herein, and with portions of an elongate sheath thereof cut away to enable enlargement of other portions of the tool.

Referring to the drawings, wherein like reference numerals represent like parts throughout the various drawing figures, reference numeral 11 is directed to a modified tool (FIGS. 3 and 4) which is a modified version of a prior art lead extraction tool 10 (FIGS. 1 and 2) known in the prior art. The modified tool 11 includes an auxiliary lever 70 which provides enhanced mechanical advantage to assist in operating a trigger assembly 30 of the tool 11. In alternative embodiments, a tool 13 (FIGS. 5 and 6), tool 15 (FIGS. 7 and 8) and a tool 17 (FIGS. 9 and 10) are provided as alternatives to enhance mechanical advantage of the user when actuating the tools 13, 15, 17. A double acting lead extraction tool 110 can be provided with or without the various levers 70, 80, 90, 100 of the tools 11, 13, 15, 17. The double acting lead extraction tool 110 acts to rotate the sheath 20 and the cutter 26 on a tip of the sheath 20, both when squeezing a trigger linkage assembly 30 and when relaxing a trigger linkage assembly 30, for enhanced operation.

Figure 2:
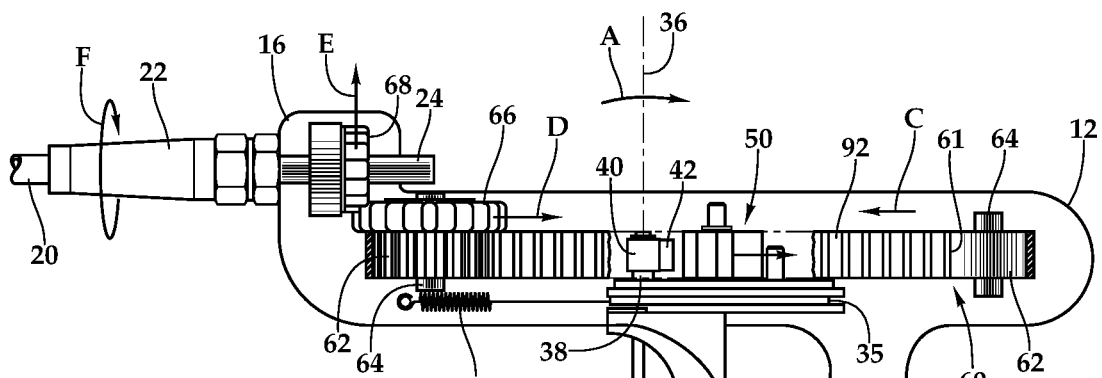
FIG. 2 is a front elevation view of that which is shown in FIG. 1, and with a rear side of a housing removed and with portions of a belt removed to reveal interior details of the prior art lead extraction tool which is modified according to various embodiments of this invention.

In essence, and with particular reference to FIGS. 2-22, basic details of the tools 11, 13, 15, 17, 110 are described, which define example embodiments of improvements on a prior art lead extraction tool 10 (FIGS. 1 and 2). The tool 11 features an auxiliary lever 70 located forward of a trigger assembly 30 extending down from a housing 12 which also supports a sheath 20 extending from a head/barrel 16 of the housing 12. The trigger assembly 30 is coupled to a mechanism, including a driver 40, a winged engager 50 and a belt 60 to cause the sheath 20 to rotate when the trigger assembly 30 is actuated. The auxiliary lever 70 is located forward of the trigger assembly 30 and pivots against the trigger assembly 30, providing mechanical advantage to a user for more easily actuating the trigger assembly 30.

With the tool 13 (FIGS. 5 and 6) a lever trigger 80 is provided which replaces the trigger assembly 30. The lever trigger 80 is attached to a shuttle 82 which replaces the driver 40 and winged engager 50. The shuttle 82 is coupled directly to a portion of the belt 60 to cause belt 60 motion when the lever 80 is actuated.

With the tool 15 (FIGS. 7 and 8) an alternative lever trigger 90 is provided which replaces the trigger assembly 30. The alternate lever trigger 90 is pivotably attached to a shuttle 92 which replaces the driver 40 and winged engager 50, with the shuttle 92 coupled directly to a portion of the belt 60 to cause the belt 60 to move when the alternate lever trigger 90 is actuated.

With the tool 17 (FIGS. 9 and 10) an inverted lever trigger 100 is provided which replaces the trigger assembly 30. Inverted lever trigger 100 is pivotably attached to a lower portion of a grip 14 of the housing 12 of the tool 17. An upper end of the inverted lever trigger 100 is coupled to a shuttle 102. The shuttle 102 replaces the driver 40 and winged engager 50, with the shuttle 102 coupled directly to a belt 60 to cause the belt 60 to move when the inverted lever trigger 100 is actuated.

The dual acting lead extraction tool 110 (FIGS. 11-22) define the mechanism which can be added to the prior art extraction tool 10 (FIGS. 1 and 2) or to the modified tool 11 (FIGS. 3 and 4), or to various other embodiments. With the tool 110, a trigger assembly 130 acts to move a double driver 140 and a pedestal 135. A rear winged engager 150 and a front winged engager 250 are supported upon the pedestal 135. Actuation of the trigger assembly 130 causes the double driver 140 to engage one of the winged engagers 150, 250 by pivoting and causing one of the winged engagers 150, 250 to engage with the belt 160 to cause the belt 160 to move, along with resulting rotation of the sheath 20 and cutter 26. Squeezing of the trigger assembly 130 causes the rear winged engager 150 to engage the belt 160 and cause the belt 160 move. When the trigger assembly 130 is released from its squeezed position, the double driver 140 engages with the front winged engager 250 to cause the front winged engager to engage with the belt 160 and cause the belt 160 to move. Thus, the double acting lead extraction tool 110 provides cutting action at a cutter 26 tip of the sheath 20, both when squeezing the trigger assembly 130 and when relaxing the trigger assembly 130.

More specifically, and with particular reference to FIGS. 3 and 4, details of the modified tool 11 are described, according to one example embodiment. This tool 11 is a modified form of the lead extraction tool 10 described above in the background, and shown in FIGS. 1 and 2. In a simplest form, the prior art tool 10 is modified into the modified tool 11 merely by adding the auxiliary lever 70 in front of the trigger assembly 30. The lever 70 is a rigid elongate structure. A pivot 72 is provided between a lower portion of the housing 12 and an upper end of a shaft 76 of the auxiliary lever 70. The shaft 76 of the auxiliary lever 70 rotates about this pivot 72 (along arrow G of FIGS. 3 and 4). The shaft 76 extends down to a tip 78 opposite the pivot 72. A link 74 is provided on a rear side of the shaft 76 which either abuts or fastens to upper portions of the trigger assembly 30.

The shaft 76 is preferably longer than the trigger assembly 30. Furthermore, because the lever 70 experiences primarily a pivoting motion (along arrow G), and because the link 74 is located closer to the pivot 72 than to the tip 76, forces applied near the tip 76 by a user have a mechanical advantage. In particular, and supposing that the link 74 is five times closer to the pivot 72 than is a portion of the shaft 76 near the tip 76, which can be easily gripped by user, five times more force would be applied to the trigger assembly 30 through the link 74 when the user squeezes the auxiliary lever 70 near the tip 78, than if the user were merely applying the same force directly to the trigger assembly 30. While a somewhat greater distance must be spanned by fingers of the user, it is a desirable trade-off to have to move the fingers further, but while applying less force, rather than to have to apply a larger force over a short distance in a highly repetitive manner. While the particular auxiliary lever 70 is shown, other levers such as those depicted in FIGS. 5-10 could alternatively be utilized along with the trigger assembly 30 to assist in utilizing the modified tool 11 according to this embodiment and related embodiments.

Figure 5:
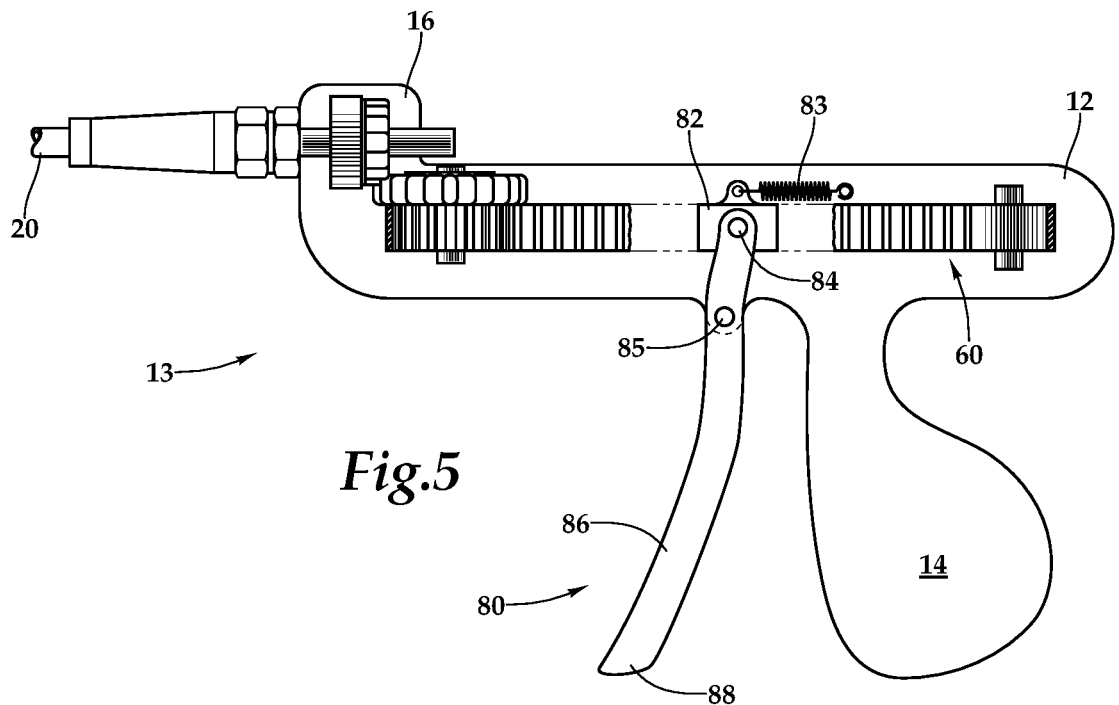
FIG. 5 is a front elevation view similar to that which is shown in FIG. 2, but with a trigger assembly replaced with a lever trigger pivotably attached to a housing of the tool and with a shuttle secured to a portion of a belt to cause corresponding rotation of the sheath and cutting tip of the tool.
Figure 6:
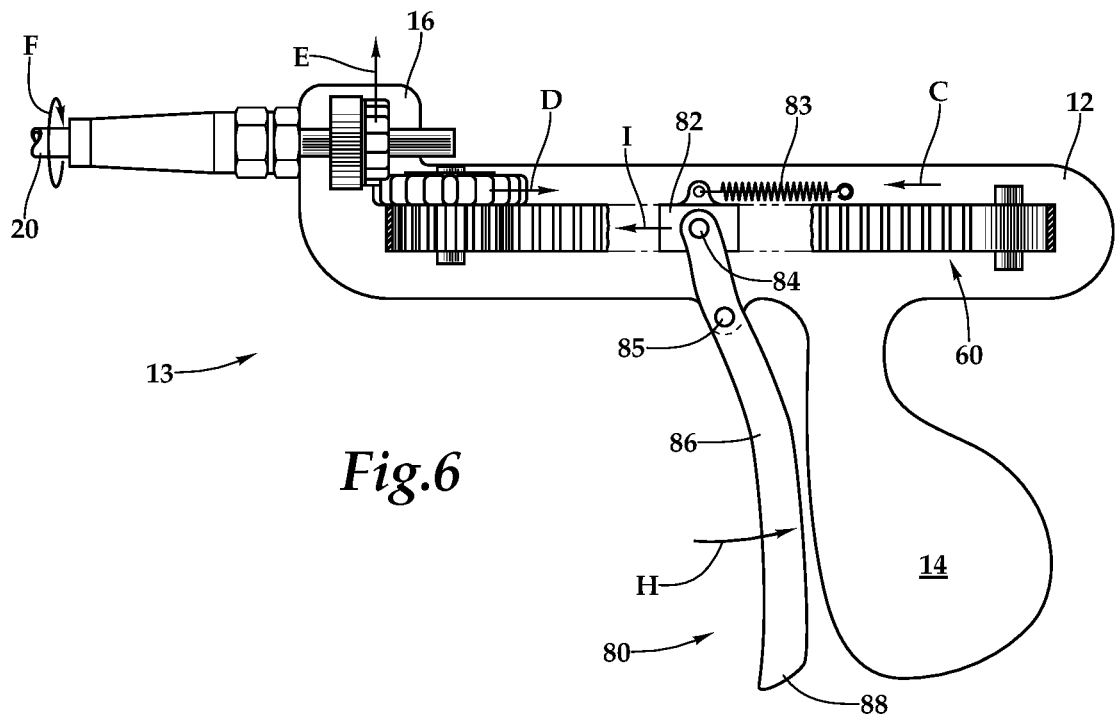
FIG. 6 is a front elevation view similar to that which is shown in FIG. 5, but with the lever trigger pivoted to a squeezed orientation and illustrating how corresponding elements within the housing respond to such lever trigger actuation.

With particular reference to FIGS. 5 and 6, details of a modified tool 13 are described, which features a lever trigger 80 in an alternative embodiment to that which is shown in FIGS. 3 and 4. With the modified tool 13, not only is the lever trigger 80 added, but the trigger assembly 30 (FIGS. 3 and 4) is removed. The driver 40 and winged engager 50 are also removed along with the trigger assembly 30. The lever trigger 80 attaches to the belt 60 through a shuttle 82. In particular, the lever trigger 80 includes an elongate shaft 86 having an upper pivot 84 through which the shaft 86 pivotably attaches to the shuttle 82, down to a tip 88 opposite the shuttle 82. The shaft 86 is also pivotally attached to the housing 12 through a housing pivot 85 located between the shuttle 82 and the tip 88. By placing the housing pivot 85 closer to the shuttle 82 than to the tip 88, forces applied near the tip 88 (along arrow H of FIG. 6) have a mechanical advantage which allows for smaller forces applied near the tip 88 to be applied onto the shuttle 82. Spring 83 is attached to the shuttle 82, or some other portion of the mechanism between the lever trigger 80 and the sheath 20.

While the belt 60 is shown as a tooth belt, the shuttle 82 can be affixed to the belt 60 in a permanent fashion so that movement of the lever trigger 80 forward and backward results in clockwise and counterclockwise motion of the sheath 20 (and associated cutter 26 at a tip of the sheath 20). The spring 83 biases the shuttle 85 toward a rearward position, so that squeezing of the lever trigger 80 (along arrow H of FIG. 6) causes a majority of the shaft 86 of the lever trigger 80 to pivot rearwardly, while upper portions of the shaft 86 above the housing pivot 85 rotate forward, causing the shuttle 82 to move (along arrow I of FIG. 6) in a forward direction.

By attaching the shuttle 82 to portions of the belt 60 on a right side of the tool 13, the belt 60 is caused to advance (along arrow C of FIG. 6), which in turn causes rotation of the input gear along arrow D and the upper gear along arrow E to result in rotation of the sheath 20 about arrow E When the lever trigger 80 is relaxed back to its original position, each of these motions is reversed, action caused by the spring 83. The cutter 26 is designed to cut in both directions, so that cutting still occurs even during the relaxing stage. Torsion springs could be associated with one of the gears between the belt 60 and the sheath 20 to allow for energy storage and/or release in various alternative embodiments.

Figure 7:
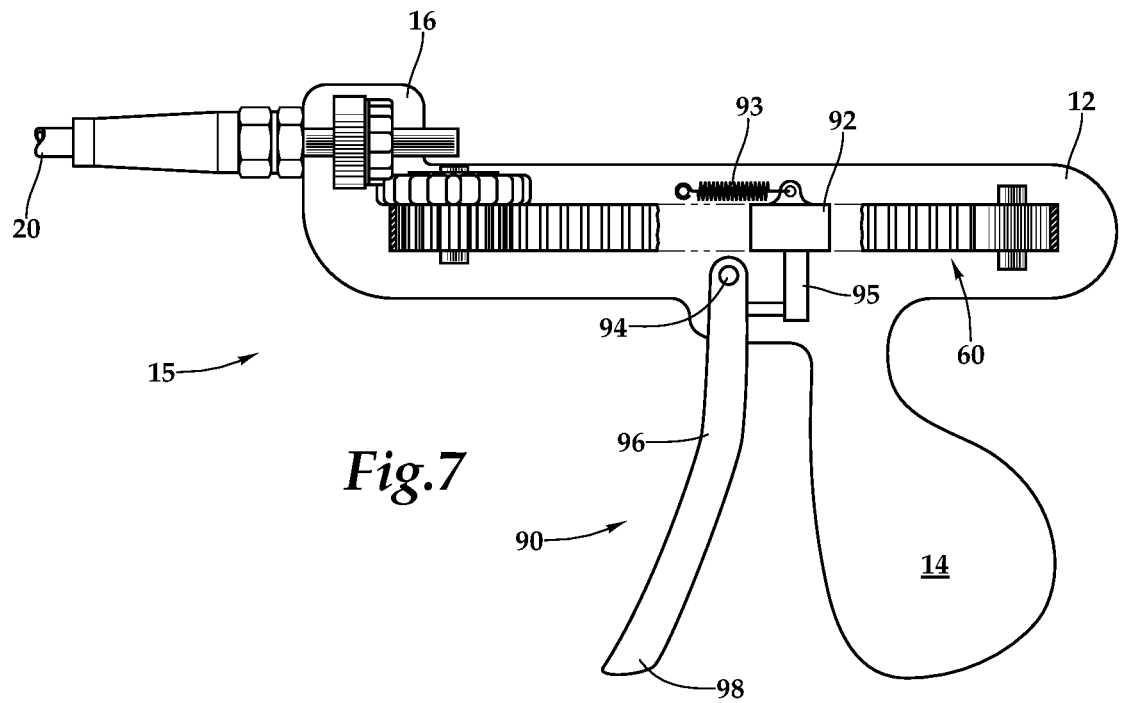
FIG. 7 is a front elevation view similar to that which is shown in FIG. 5, but with an alternate lever trigger which is attached to the shuttle and belt in a manner which causes a reverse direction of motion of the belt relative to that depicted in FIGS. 5 and 6.
Figure 8:
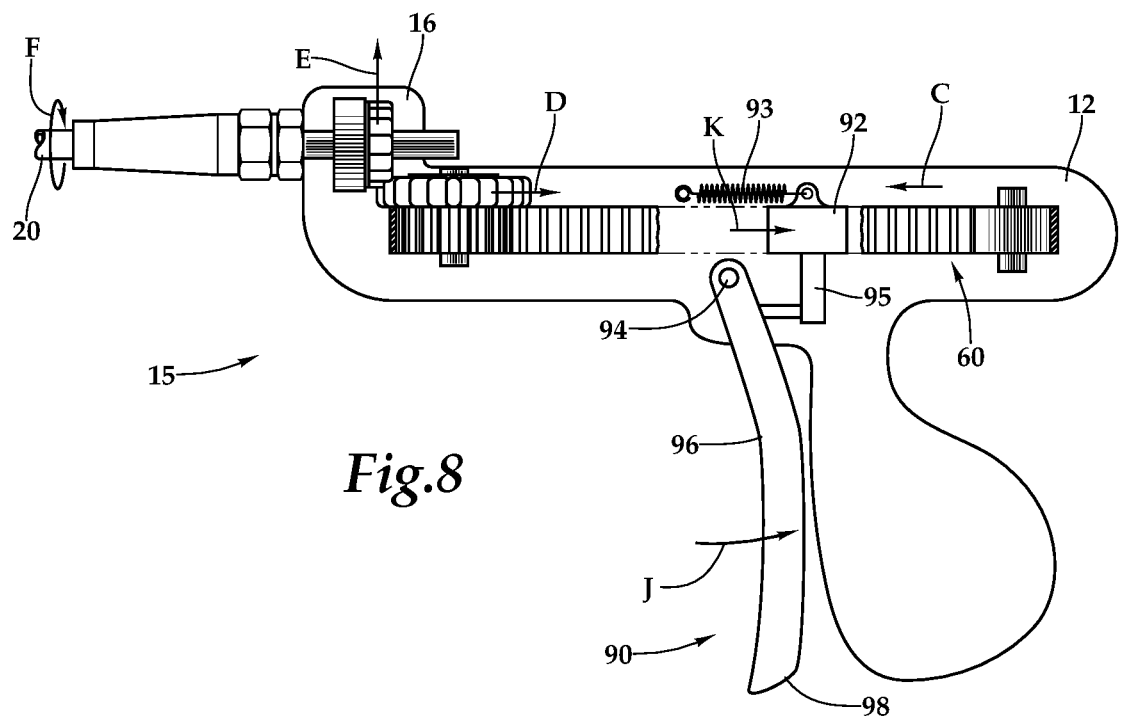
FIG. 8 is a front elevation view of that which is shown in FIG. 7, but with the alternate lever trigger actuated and showing corresponding mechanisms within the housing responding correspondingly.

With particular reference to FIGS. 7 and 8, details of a modified tool 15 featuring an alternate lever trigger 90 are described, according to one embodiment. The tool 15 is similar to the modified tool 13, except that the alternate lever trigger 90 replaces the lever trigger 80. Alternate trigger 90 includes a shuttle 92 coupled to the belt 60. A shaft 96 replaces the trigger assembly 30 (of the prior art tool 10 of FIGS. 1 and 2). The shaft 96 extends from an upper pivot 94, pivotably attached to the housing 12 of the tool 15, down to a tip 98 opposite the upper pivot 94. A linkage 95 behind the shaft 96 couples the shaft 96 to the shuttle 92.

The spring 93 biases the shuttle 92 toward a forward position. When the alternate lever trigger 90 is squeezed (along arrow J of FIG. 8) the shuttle 92 is caused to move rearwardly (along arrow K of FIG. 8). With the shuttle coupled to a left side of the belt 60, this causes the belt to move with the right side of the belt moving forward, along arrow C of FIG. 8. This in turn causes the pair of gears to move along arrows D and E, and causing the sheath to rotate about arrow E As with other embodiments, springs in other positions and of different types could alternatively bias the shuttle 92 or other portions of the mechanism to cause the lever 96 of the alternate lever trigger 90 to return to an original position when squeezing forces are removed.

Figure 9:
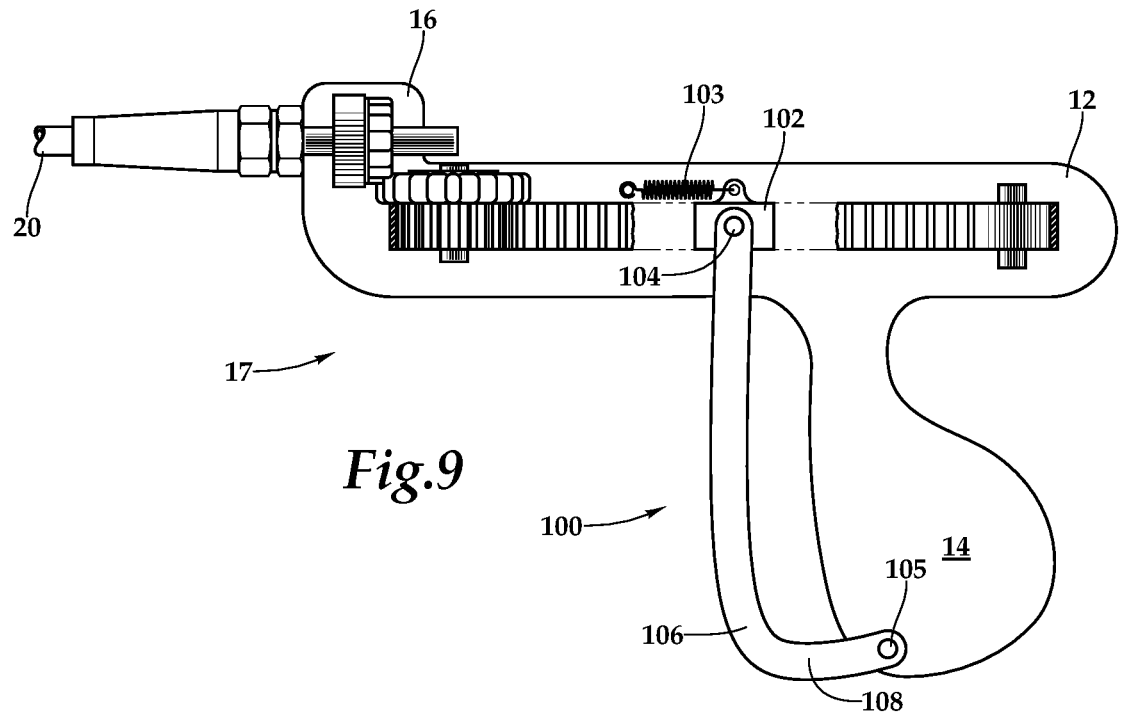
FIG. 9 is a front elevation view similar to that which is shown in FIG. 5, but with an inverted lever trigger physically attached to a grip of the tool and also to a shuttle of the tool.
Figure 10:
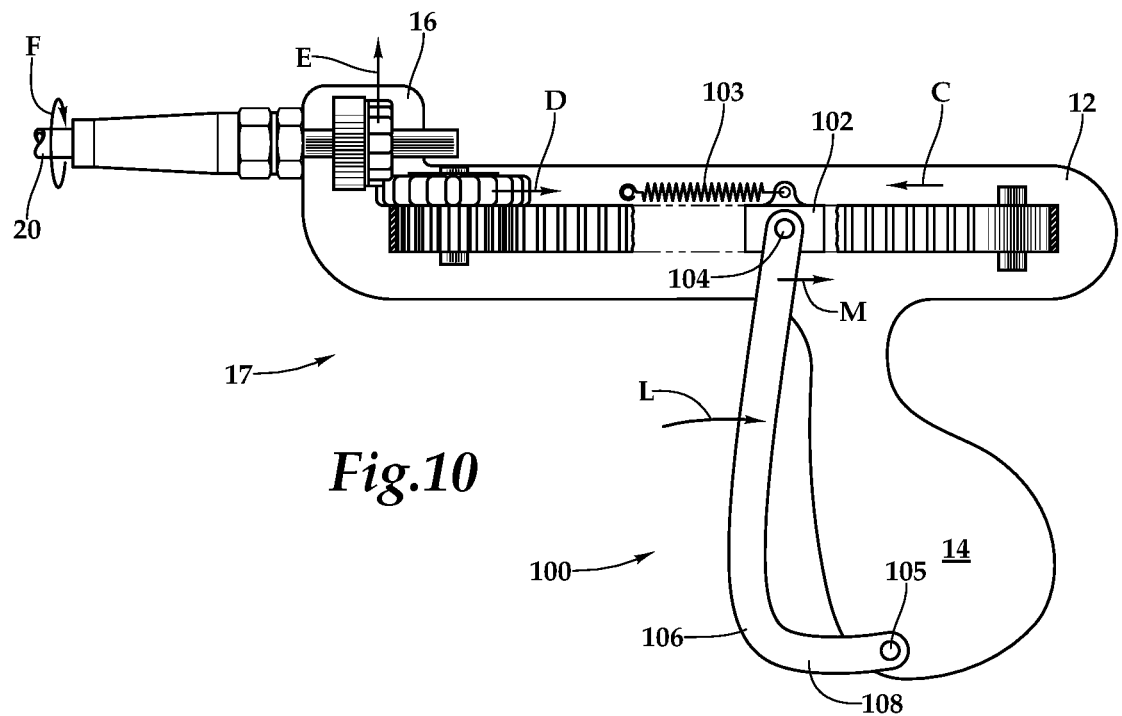
FIG. 10 is a front elevation view similar to that which is shown in FIG. 9, except with the inverted lever trigger having been actuated, revealing how corresponding elements within the tool respond to such inverted lever trigger actuation.

With particular reference to FIGS. 9 and 10, details of a modified tool 17 featuring an inverted lever trigger 100 are described, according to one embodiment. The inverted lever trigger 100 replaces the trigger assembly 30 of the prior art tool of FIGS. 1 and 2. This inverted lever trigger 100 includes a bent shaft 106 which is coupled to a shuttle 102 at an upper pivot 104. The shuttle 102 is secured to the belt 60, similar to other embodiments depicted in FIG. 5-8. The inverted lever trigger 100 features the bent shaft 106 which pivots to the grip 14 through a grip pivot 105 near a tip 108 of the bent shaft 106. The bent shaft 106 has a bend about ¾ of the way between an upper pivot 104 at the shuttle 102 and the grip pivot 105.

When the bent shaft 106 of the inverted lever trigger 100 is squeezed (along arrow L of FIG. 10), this in turn causes the shuttle 102 to move rearwardly (along arrow M of FIG. 10). With the shuttle 102 secured to the belt on a left side of the belt, such motion of the shuttle 102 along arrow M causes the belt to move along arrow C of FIG. 10. This in turn causes the pair of gears to move along arrows D and E and in turn causes the sheath 20 to rotate about arrow E While the spring 103 is shown as a linear tension spring biasing the shuttle 102 and bent shaft 106 of the inverted lever trigger 100 toward an original position, other arrangements of springs could be provided, as with other embodiments.

With the inverted lever trigger 100 of the tool 17, as well as the other modified tools 13, 15 which utilize a shuttle 82, 92, 102, it is conceivable that the belt 60 could be replaced with a rack gear. Such a rack gear could act directly upon the input gear 66 or the output gear 68 could be replaced with a worm gear. Other forms of gear mechanisms could replace the belt 60 in various different embodiments and still provide direct translation of linear motion of the shuttles 82, 92, 102 into rotation of the sheath 20 (and the associated cutter 26). As another alternative, the shuttles 82, 92, 102 could merely be replaced with having upper ends of the various shafts 86, 96, 106 directly coupled to the belt 60, such as with a rivet.

Various tools 11, 13, 15, 17 could additionally include a helical torsion spring associated with the input gear 66 or associated with one of the pulleys (or both of the pulleys). With a clutch or other engagement/disengagement mechanism between the belt 60 and a portion of such a pulley or gear which has such a torsion spring associated therewith, energy could be stored in such a torsion spring in a first mode. Then in a second mode energy stored within the spring could be released.

A manual switch could engage/disengage such a clutch to store/release energy when desired. For instance, a user could squeeze the trigger repeatedly in a first mode where the sheath is kept from rotation, and the helical torsion spring and/or clock spring would store up energy. In a second mode of operation, the sheath would be engaged with the gears and a clutch or other brake could be regulated to allow energy from the helical torsion spring and/or clock spring to be output to the sheath 20 to cause rotation of the sheath 20 and associated cutter 26 under control of the user.

When the energy has been used up, the process could be repeated. In this way, a user would not have to be both exerting energy and exercising care and skill at the same time. Rather, first energy would be exerted to store up energy within the tool. Then, the skilled surgeon or other medical professionals could control the release of the energy while applying the appropriate amount of pressure through the sheath 20 and upon the cutter 26, while also carefully managing tension in the lead wire, so that optimal freeing of the lead wire is achieved with the upmost care and with all exertion of the user going into exercising of appropriate care, rather than powering the tool 11, 13, 15, 17 manually at the same time.

With particular reference to FIGS. 11-22, details of the double acting lead extraction tool 110 are described, according to one embodiment. The double acting lead extraction tool 110 could be provided as a modification to the lead extraction tool 10 of the prior art (FIGS. 1 and 2), or could be provided along with a modified tool 11 which features the auxiliary lever 70, or can be provided on some other similar lead extraction tool 10, or as a standalone newly developed tool having at least some attributes similar to those of the lead extraction tool 10 of the prior art.

The double acting lead extraction tool 110 includes a housing 112 with a grip 114 and head/barrel 116 which are similar to corresponding structures of the lead extraction tool 10 of the prior art (FIGS. 1 and 2). Furthermore, a trigger assembly 130 of the double acting lead extraction tool 110 is similar to the trigger assembly 30 of the lead extraction tool 10, and including a sliding main trigger 132 along with a pivoting trigger 134. The pivoting trigger 134 causes a trigger axis 136 to pivot (about arrow A of FIG. 14). The trigger assembly 130 also includes a pedestal 135 which is biased by spring 137 toward a forward position. Bias spring 139 biases the pivoting trigger 134 away from the sliding main trigger 132. The sliding main trigger 132 is attached to the pedestal 135, so that when the sliding main trigger 132 is slid rearwardly (along arrow B of FIG. 16), pedestal 135 is also caused to move rearwardly.

As an option with this embodiment, a selector knob 120 is provided extending along the trigger axis 136 and up out of an upper portion of the housing 112. The selector knob 120 is on an upper end of a long rod 122 extending along the trigger axis 136. The selection knob 120 can be rotated (along arrow N of FIGS. 11 and 12). Such rotation will cause a double driver 140 to be either in a first position or a second position which correspond with rotation of the output shaft 124 associated with the sheath in either a clockwise direction or a counterclockwise direction (along arrow F or opposite arrow F of FIG. 16).

The double driver 140 is similar to the driver 40 of the prior art lead extraction tool 10 (FIGS. 1 and 2) except that it has a forward point 142 and a rearward point 144, rather than only a point 42 pointing in a rearward direction, in the case of the prior art lead extraction tool 10. With such a forward point 142 and a rearward point 144, the double driver 140 is configured so that it can engage with both a rear winged engager 150 behind the double driver 140 or with a front winged engager 250 in front of the double driver 140, and to facilitate rotation of the output shaft 124 and sheath 20, both when the trigger assembly 130 is squeezed and when it is relaxed.

The rear winged engager 150 is preferably similar to the winged engager 50 of the extraction tool 10 of the prior art. This rear winged engager 150 thus includes a body 152 carried upon a pivot pin 154, and with the body 152 carried by the pedestal 135 through the pivot pin 154. In this way, when the pedestal 135 slides (along arrow B of FIGS. 15 and 16), the body 152 and pivot pin 154 move along with the pedestal 135. A forward portion of the body 152 features a nose 153 thereon which interacts with the rearward point 144 of the double driver 140 when the double driver 140 moves rearwardly (along arrow A of FIGS. 13 and 14).

A pair of wings 156 are pivotably attached to the body 152 in a manner which is biased to have the wings 156 spread outwardly away from each other and toward left and right sides of the belt 160, so that tips of the wings 156 can reach and engage with certain ones of the teeth 161 of the belt 160. By biasing the wings 156 with springs and pivoting them, the wings 156 can only engage with the teeth 161 of the belt 160 when the tip of one of the wings 156 is engaging with a tooth 161 of the belt 160 and the entire rear winged engager 150 is moved rearwardly along with motion of the pedestal 135 (along arrow B of FIGS. 15 and 16). This causes the belt 160 to move (along arrow C of FIGS. 15 and 16).

The belt 160 is carried upon pulleys 162 which rotate upon axles 164. A forward one of the pulleys 162 has an input gear 166 associated therewith. An output gear 168 is oriented perpendicular to the input gear 166 and with teeth of the output gear 168 meshing with teeth of the input gear 166. The output gear 168 supports the output shaft 120 for the output shaft 124 to turn, and then in turn to cause the sheath 20 and cutter 26 (FIGS. 1 and 2) to rotate about arrow F.

Under bearings 170 and lateral bearings 180 are depicted in FIGS. 21 and 22. These bearings 170, 180 are adjacent to sides of the pedestal 135 and under the pedestal 135 to slide with minimal friction between a rearward and a forward position. Similarly, bearings can be associated with the pulleys 162, such as through the axles 164, so that energy is not wasted overcoming friction. Wheels could also be used or replace the bearings to minimize friction and associated wasted friction by the use of the tool 10.

Importantly with this invention, a front winged engager 250 is also provided, mounted upon the pedestal 135 and on a portion of the pedestal 135 forward of the double driver 140. In one embodiment, the front winged engager 250 is identical to the rear winged engager 150, except it is reversed in orientation. Thus, the front winged engager 250 has the body 252 pivotably supported upon a pivot pin 254 to a forward portion of the pedestal 135. Wings 256 extend laterally from the body 252 and are pivotally attached to the body 152 and spring biased toward positions away from each other. A nose 253 points rearwardly from the body 252 and toward the double driver 140. The nose 253 and body 252 interact with the forward point 142 on the double driver 140 to cause the front winged engager 250 to be rotated somewhat about the pivot pin 254 and to cause one of the wings 256 to engage with teeth 161 on the belt 160, to in turn cause motion of the belt 160 (such as along arrow X of FIG. 21), when the trigger assembly 130 is returning to an original position along arrow W of FIGS. 21 and 22.

In use and operation, and considering FIGS. 11-22 sequentially, details of the operation of the dual acting lead extraction tool 110 are described, according to one embodiment. Initially, the trigger assembly 130 is in a forward position and the spring 137 is relaxed, and the bias spring 139 is relaxed. In fact, the bias spring 139 can have some energy remaining therein and the spring 137 can have some energy remaining therein in some embodiments. Initial position for the double driver 140 can be similar to that depicted in FIG. 11. However, if a selector knob 120 is provided, it can be rotated (about arrow N of FIGS. 11 and 12) to cause the double driver 140 to have a rotational orientation either similar to that depicted in FIG. 11 or similar to that depicted in FIG. 13. The one selected orientation will cause the first rotation of the cutter 26 at the tip of the sheath 20 to be clockwise, while the other position will cause such a rotation to be counterclockwise. Markings on the selector knob 120 can correspond with the rotation which will occur, so that a user can have control over whether the first rotation of the cutter 26 will be clockwise or counterclockwise.

In the example shown in FIGS. 11 and 12, the double driver 140 is in a position with its rearward point 144 slightly left of center (when looking down and forward) and with the double driver 140 having its forward point 142 slightly right of center. A user first squeezes the trigger assembly 130, which causes the pivoting trigger 134 to pivot (along arrow A) and causing the double driver 140 to move rearwardly and engage the rear winged engager 150. In particular, the rearward point 144 of the double driver 140 impacts the nose 153 and body 152 of the rear winged engager 150. Such engagement involves surfaces of the body 152 of the rear winged engager 150 and surfaces of the rearward point 144 of the double driver 140 interacting to cause mutual opposite rotations, with the driver rotating about arrow P and the rear winged engager 150 rotating about arrow Q (FIG. 13). Such rotation of the rear winged engager 150 causes a left wing of the rear winged engager 150 to engage with teeth 161 of the belt 160 at a left side of the belt 160.

Figure 15:
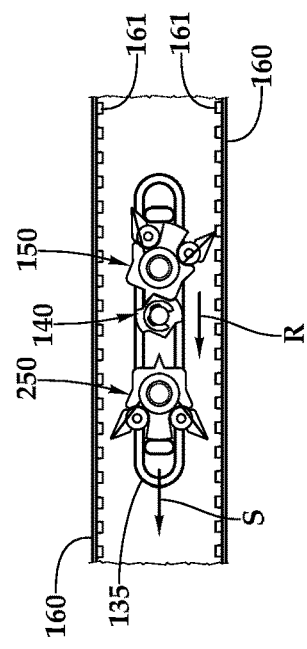
FIG. 15 is a top plan view similar to that which is shown in FIG. 13, but after the trigger assembly has been fully squeezed and the belt caused to be advanced.
Figure 16:
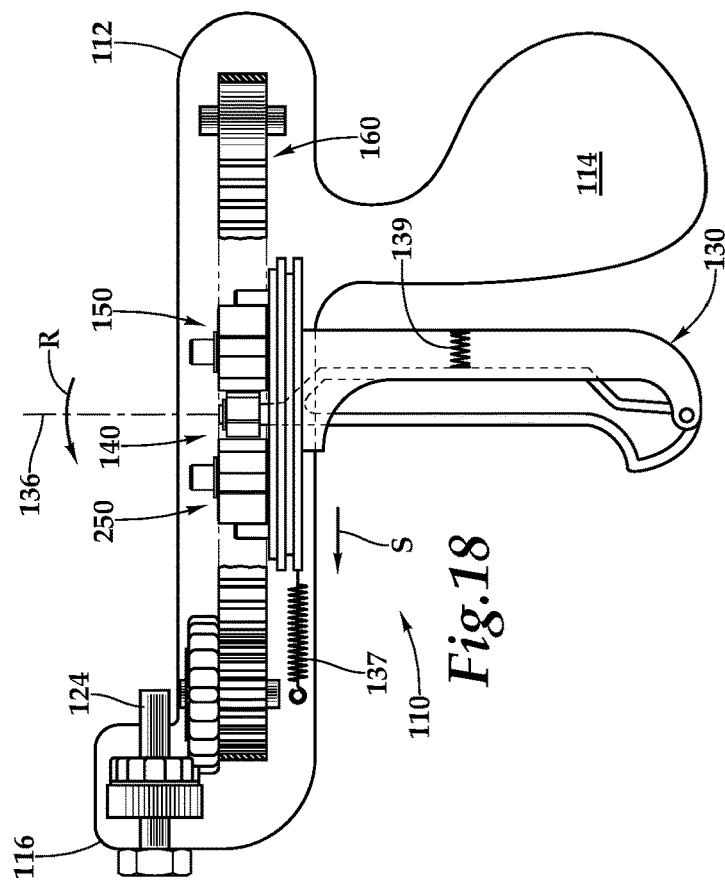
FIG. 16 is a front elevation view that which is shown in FIG. 15, and also including surrounding elements of the entire tool other than the sheath.

With particular reference to FIGS. 15 and 16, further squeezing of the trigger assembly 130 causes the sliding main trigger 132 to slide rearwardly (along arrow B of FIGS. 15 and 16). This causes the pedestal 135 to move rearwardly. Because the left wing on the rear winged engager 150 is engaged with teeth 161 on the belt 160, the left side of the belt 160 is caused to move rearwardly (along arrow C of FIG. 15) which causes corresponding forward motion of the belt 160 along a right side of the belt 160 (along arrow C of FIG. 15). This in turn causes corresponding rotation of the input gear 166 along arrow D and corresponding rotation of the output gear 168 along arrow E, and rotation of the output shaft 124 along arrow F (FIG. 16). Together this action to rotate the sheath 20 involves action of the squeeze engaging linkage between the trigger assembly 130 and the sheath 20. One form of squeeze engaging linkage is the double driver 140 and the rear winged engager 150. At this point, half of a full cycle of operation of the dual acting lead extraction tool 110 has occurred.

Figure 17:
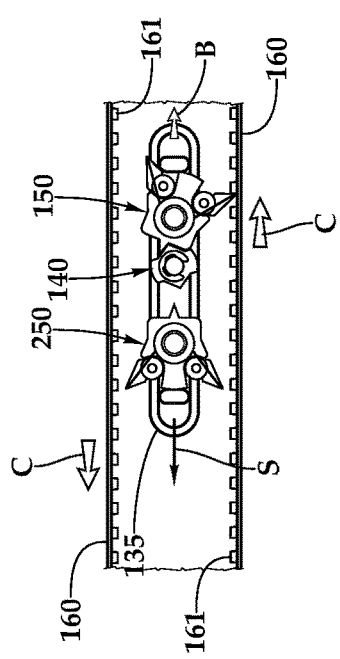
FIG. 17 is a top plan view of that which is shown in FIG. 15, but after the trigger assembly has begun to move forwardly at the end of the squeeze stroke and at least partially under force of at least one spring.
Figure 18:
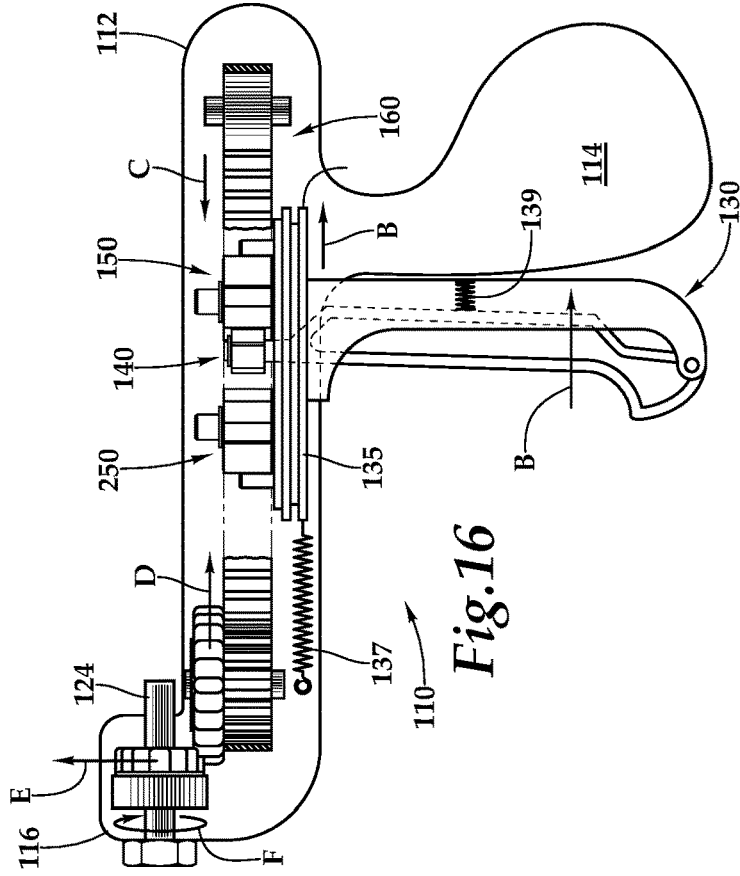
FIG. 18 is a front elevation view of that which is shown in FIG. 17 and also includes surrounding elements of the entire tool other than the sheath.

With reference to FIGS. 17 and 18, a user next relaxes slightly a grip on the trigger assembly 130, and the spring 137 releases tension energy stored therein to pull the pedestal 135 forward slightly (along arrow S of FIGS. 17 and 18), and also (typically just after) the double driver 140 to be brought back to upright (along arrow R of FIGS. 17 and 18). In various different embodiments, motion along arrow S could occur before motion along arrow R, or motion long arrow R could occur before motion long arrow S. Initial motion along arrow S is preferably very limited, or no motion along arrow S occurs at all at this initial stage, but rather only rotation long arrow R. The double driver 140 holds its rotational orientation which it had within FIG. 15, so that the forward point 142 is slightly left of center.

With a particular reference to FIGS. 19 and 20, as the trigger assembly 130 continues to be released by a user, further motion of the pivoting trigger 134 and rotation along arrow T, causes the double driver 140 forward point 142 to engage with the front winged engager 250. This action is driven by the bias spring 139. In one embodiment, this bias spring 139 can be turned or deactivated with a selector to keep the pivoting trigger 134 from pivoting forward of vertical and to keep the double driver 140 from engaging the rear winged engager 250. In such a setting, the dual action of the tool is disengaged and only squeezing action results in sheath 20 rotation. This engagement and the various surfaces of the forward point 142 of the double driver 140 and the nose 253 and body 252 of the front winged engager 250 cause mutual rotation of the double driver 140 along arrow U (FIG. 19) and front winged engager 250 along arrow V (FIG. 19). This in turn causes a left wing 256 of the front winged engager 250 to engage with teeth 161 on a left side of the belt 160.

With particular reference to FIGS. 21 and 22, further releasing of the trigger assembly 130 causes sliding of the sliding main trigger 132 (along arrow W of FIGS. 21 and 22) which carries the pedestal 135 forwardly while the front winged engager 250 is engaged with a left side of the belt 160 (unless the bias spring 139 and/or other selector has kept the double driver from engaging the front winged engager 250, in which case the trigger 130 merely returns to reset the trigger for another squeeze). Thus, as the pedestal 135 moves forward along with the trigger assembly 130, the left side of the belt 160 is caused to move forward (along arrow X of FIG. 21) which in turn causes rotation of the input gear 166 along arrow Y and the output gear 168 along arrow Z, and rotation of the output shaft 124 about arrow a. Such mechanism action involves what can be considered a relax engaging linkage including the double driver 140 and front winged engager 250.

Note that in FIGS. 21 and 22 the double driver 140 and the rear winged engager 150 and front winged engager 250 are ready for motion associated with squeezing of the trigger assembly 130, and as depicted in FIGS. 11-14, to repeat the process with a further cycle. At any stage in the process, the selector knob 120 can be rotated, such as if it is desired to keep the cutter 26 rotating in a clockwise direction or keep the cutter 26 rotating in a counterclockwise direction, rather than going back-and-forth between clockwise and counterclockwise rotation.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A manual cardiac lead extraction tool, comprising in combination:
   a barrel with a sheath extending therefrom to a lead extraction cutter tip, with axial rotation of the sheath producing axial rotation of said cutter tom;
   a handle grippable by at least a portion of a hand of a user;
   a trigger adjacent to said handle, said trigger movable toward and away from said handle by squeezing or relaxing said trigger;
   an output shaft coupled to the sheath;
   a moveable belt being located between said trigger and said sheath;
   said trigger operatively coupled to said output shaft through a squeeze engaging linkage in a manner enabling a translation of said trigger toward said handle to impart rotation on said output shaft, said sheath and said cutter tip;
   said trigger operatively coupled to said output shaft through a relax engaging linkage in a manner enabling a translation of said trigger away from said handle to impart rotation on said output shaft, said sheath and said cutter tip; and
   wherein said squeeze engaging linkage is oriented to engage said belt when said trigger is squeezed, and wherein said relax engaging linkage is oriented to engage said belt when said trigger is relaxed.

2. The tool of claim 1 wherein a spring biases said trigger toward an unsqueezed position more distant from said handle than a squeezed position for said trigger.

3. The tool of claim 2 wherein said trigger is longer than said handle and said trigger pivots as it moves relative to said handle, with a distal tip opposite a pivot.

4. The tool of claim 1 wherein said squeeze and relax engaging linkages are identical, oriented with opposite orientations relative to each other and positioned to engage the belt which is coupled indirectly to said sheath.

5. The tool of claim 4 wherein said belt includes a plurality of inwardly facing teeth, and with said squeeze and relax engaging linkages having wings thereon which engage said teeth of said belt when said trigger is moved in either a squeezing or relaxing manner for engagement of one of said squeeze and relax engaging linkages with said belt.

6. The tool of claim 4 wherein said squeeze and relax engaging linkages can be switched through actuation of an engagement selector, controlling a direction in which said sheath rotates upon both squeezing and relaxing actions of said trigger.

7. The tool of claim 4 wherein said squeeze and relax engaging linkages causes rotation of said sheath and said cutter tip in opposite directions.

8. The tool of claim 1 wherein said relax engaging linkage can be disengaged to deactivate the relax engaging linkage, such that one-way operation of the trigger upon squeezing and without operation upon relaxing can occur.

9. The tool of claim 1 wherein wheels are included in said squeeze and relax engaging linkages to reduce friction associated with motion of at least one of said trigger, said squeeze and relax engaging linkages or said belt.

* * * * *